United States Patent [19]

Constantin

[11] Patent Number: 4,836,013
[45] Date of Patent: Jun. 6, 1989

[54] DEVICE INTENDED FOR TESTING THE MECHANICAL STRENGTH OF PRESSURIZED CONTAINERS IN A HOT CONDITION

[75] Inventor: Daniel Constantin, Paris, France
[73] Assignee: L'Oreal, Paris, France
[21] Appl. No.: 109,262
[22] Filed: Oct. 14, 1987
[30] Foreign Application Priority Data
   Oct. 31, 1986 [FR] France .................. 86 15173
[51] Int. Cl.⁴ .......................................... G01M 3/04
[52] U.S. Cl. .................................. 73/41; 73/49.3; 73/52
[58] Field of Search ............ 374/45, 57, 5; 73/41, 73/45.4, 49.3, 52, 41.2, 40, 39

[56] References Cited

U.S. PATENT DOCUMENTS

| | | | |
|---|---|---|---|
| 3,350,919 | 11/1967 | Mucci et al. | 73/41.2 |
| 3,729,984 | 5/1973 | Waldherr | 73/52 |
| 3,757,587 | 9/1973 | Ahnsorge | 73/45.4 |
| 3,950,982 | 4/1976 | Bade et al. | 73/45.5 |

FOREIGN PATENT DOCUMENTS 996830  6/1965  United Kingdom .............. 73/41.2

Primary Examiner—Stewart J. Levy
Assistant Examiner—Herron E. Williams
Attorney, Agent, or Firm—Cushman, Darby & Cushman

[57] ABSTRACT

The device comprises a conveyor for displacing the containers to be tested in translation in relation to a tunnel-shaped fixed enclosure and comprising internally a heating means. This heating means is constituted by a plurality of infrared lamps each of which is protected by a casing having a side transparent to the radiation emitted. An automatic monitoring device checks that each container entering the tunnel leaves it after a given advance of the conveyor, otherwise a safety device is triggered. The device can be used for testing the mechanical strength of pressurized containers of the aerosol can type on a continuous production line.

15 Claims, 3 Drawing Sheets

DEVICE INTENDED FOR TESTING THE MECHANICAL STRENGTH OF PRESSURIZED CONTAINERS IN A HOT CONDITION

FIELD OF THE INVENTION

The present invention relates to a device for continuous testing of the mechanical strength of pressurized containers, in particular of the "aerosol can type", in a hot condition.

Containers of this type are used for example for storing and dispensing cosmetic or maintenance products; such containers are provided with a dispensing valve enabling the user to eject the product to be dispensed by pressing on the push button provided with a valve.

PRIOR ART

Once the products have been introduced it is necessary to test the containers to ascertain whether they have a sufficient mechanical strength to withstand the storage pressure in all the usual storage conditions. For this purpose, the containers are disposed on a conveyor and they are made to pass into a hot water bath being left therein for a sufficiently long time to be brought to a core temperature at approximately 50°-55° C.

This currently used technique has the drawback of requiring a relatively high energy consumption to maintain the water bath at the desired temperature. Moreover, if the external surface of the container wall is not completely smooth and therefore has a tendency to retain the water (as in the case of the valve cup which always retains some water or of containers whose wall is made of ground glass, possibly covered with a matt paint) it is necessary to carry out an additional operation of drying the containers when they leave the bath, because the normal drying time in free air would be far too long and would adversely affect the proper working of the packaging lines.

OBJECTS OF THE INVENTION

It is an object of the present invention to overcome the above-mentioned drawbacks.

It is a further object of the invention to provide a testing device in which the pressurized containers are exposed to heating radiation, for example infrared, for very rapidly heating the gaseous phase constituting the propellant so as to bring the containers to an internal pressure equivalent to that attained when they are brought to a core temperature of 50°-55° C.

It is a further object of the invention to avoid any risk of fire due to the splashing of the contents of a container on to a lamp following the breakage of this container, and this is achieved by enclosing each of the lamps in a ventilated and pressurized leakproof casing advantageously in adjustable positions.

The twofold problem which has occurred, is resolved by the invention because the choice of infrared radiation for heating the containers to be tested makes it possible to obtain a better control of the energy expenditure; in particular, provision can be made for stopping the conveyor and turning the lamps off if, after a given time, no container is leaving the tunnel because of a jam inside the tunnel, or if no container is presented at the inlet of the tunnel. There is no reason for drying the containers after the test since the containers are no longer wet.

SUMMARY OF THE INVENTION

The present invention provides a device intended for the continuous testing of the mechanical strength of each pressurized container of a series of pressurized containers, in a hot condition, this device comprising a conveyor for displacing the containers to be tested in translation in relation to a fixed enclosure which comprises internally a heating means, the containers traversing the enclosure so that their internal temperature should be raised by the said heating means up to a predetermined value, characterized in that the enclosure traversed by the containers to be tested forms a tunnel, the heating means disposed within the enclosure being constituted by a plurality of infrared lamps, each one of which is protected by a casing having a face which is transparent to the radiation emitted, an automatic monitoring device ensuring that each container which enters the tunnel emerges therefrom after a given advance of the conveyor, in the absence of which, a safety device is triggered.

The number of lamps and their disposition on the packaging line (either opposite one another or staggered in relation to each other) depends on the instantaneous flow of the packaging line, the dimensions of width of the containers, and the time necessary for obtaining inside the container a pressure equivalent to that reached when they are brought to the temperature of the above-mentioned test.

The lamps are disposed in a tunnel constituted, for example, by detachable cases mounted on a chassis, these cases being thermally insulated, an inlet window and an outlet window being arranged for the containers. The tunnel is traversed by a conveyor which displaces the containers.

The invention provides the advantage that it is possible to use a conveyor not comprising the mechanical container holding means, which were necessary with use of a hot water bath. In the case of the present ., if the containers are unstable on their base, t₁  simply be placed into a bucket carried by the conveyor.

Moreover, the strength test can be effected in more straightforward and reliable conditions than with the prior art. In fact, with a device according to the invention, the push button, and possibly the caps, can be positioned on the containers before the test; this could not be done in the prior art because water would have remained in the vicinity of the cap or the push button. In the case of a water bath, it was, therefore, necessary to attach the push button or cap after the test, which operation was hampered by the fact that the seal of the valve stem is expanded while the container is still hot.

The present invention also offers advantages from the point of view of safety because, since the containers are conveyed in a tunnel, the contents are not splashed on to the operators if one of them bursts. Moreover, any anomalies which can occur in the tunnel can be detected so that if one of the containers that had entered into it is not found at the outlet at the appropriate time, the operation of the infrared lamps and of the conveyor can be stopped immediately.

In one embodiment of the present invention, the outlet of the tunnel is fitted with a protective deflector, slanting in relation to the axis of the outlet, the conveyor following the contour of the said deflector after emerging from the tunnel, the orientation of the deflector being related to the installation of the tunnel on the production line.

Moreover, the casing associated with each infrared lamp is a cooled metallic casing, the face which is transparent to the infrared radiations comprising on the one hand, a quartz strip towards the inside of the casing and on the other hand a glass strip impervious to thermal shocks towards the outside of the casing, the space between the strips being preferably swept by a cooling fluid advantageously constituted by a flow of compressed air. Moreover, each infrared lamp casing is preferably provided with external cooling fins.

In accordance with an advantageous characteristic of the present invention, the median line of the conveyor is U-shaped, the entry of the containers into the enclosure being effected via one of the arms of the U and the emergence via the other arm, the infrared lamps being disposed on either side of the conveyor all along the path of the conveyor in the enclosure. The median line of the conveyor can also be substantially rectilinear.

The monitoring device may advantageously comprise means indexing the advance of the conveyor step by step and, at the inlet and outlet of the enclosure, detector means for determining the presence or absence of a pressurized container over a zone having the length of one step of the advance of the conveyor. These indexing and detector means are notably optical transmitter-receivers. In particular, each optical transmitter-receiver comprises (a) a photodiode associated with a bundle of optical fibres whose end is fixed in relation to the detector means which is displaced by the conveyor and (b) situated opposite the end of the first fibre bundle another optical fibre bundle connected to a receiving phototransistor.

In a preferred embodiment of the monitoring device, the indexing means which it comprises supplies one pulse when one slot of a slotted wheel passes a fixed point, which wheel is integral with the driving drum for the conveyor, the passing of one slot to another corresponding to one indexing step of tl advance of the conveyor. Thus, the means for detec ng the entry and emergence can be adapted to supply, as each container is registered, a rectangular wave voltage signal which is of a shorter duration than the interval separating two successive pulses of the indexing means. Advantageously, the rectangular wave signals of the entry detection means are fed to a register with time delay where they are displaced by one stop at each impulse received from the indexing means, the signal level at one point of the register which corresponds, starting from the entry into the register, to the number of advance steps separating the entry and emergence detections, being compared with the level of the signal detected at the outlet.

BRIEF DESCRIPTION OF THE DRAWINGS

To render the present invention more readily understood, an embodiment is represented in the attached drawings and will be described below by way of a purely illustrative and non-restrictive example.

In these drawings.

DESCRIPTION OF THE PREFERRED EMBODIMENT

Figure 1:
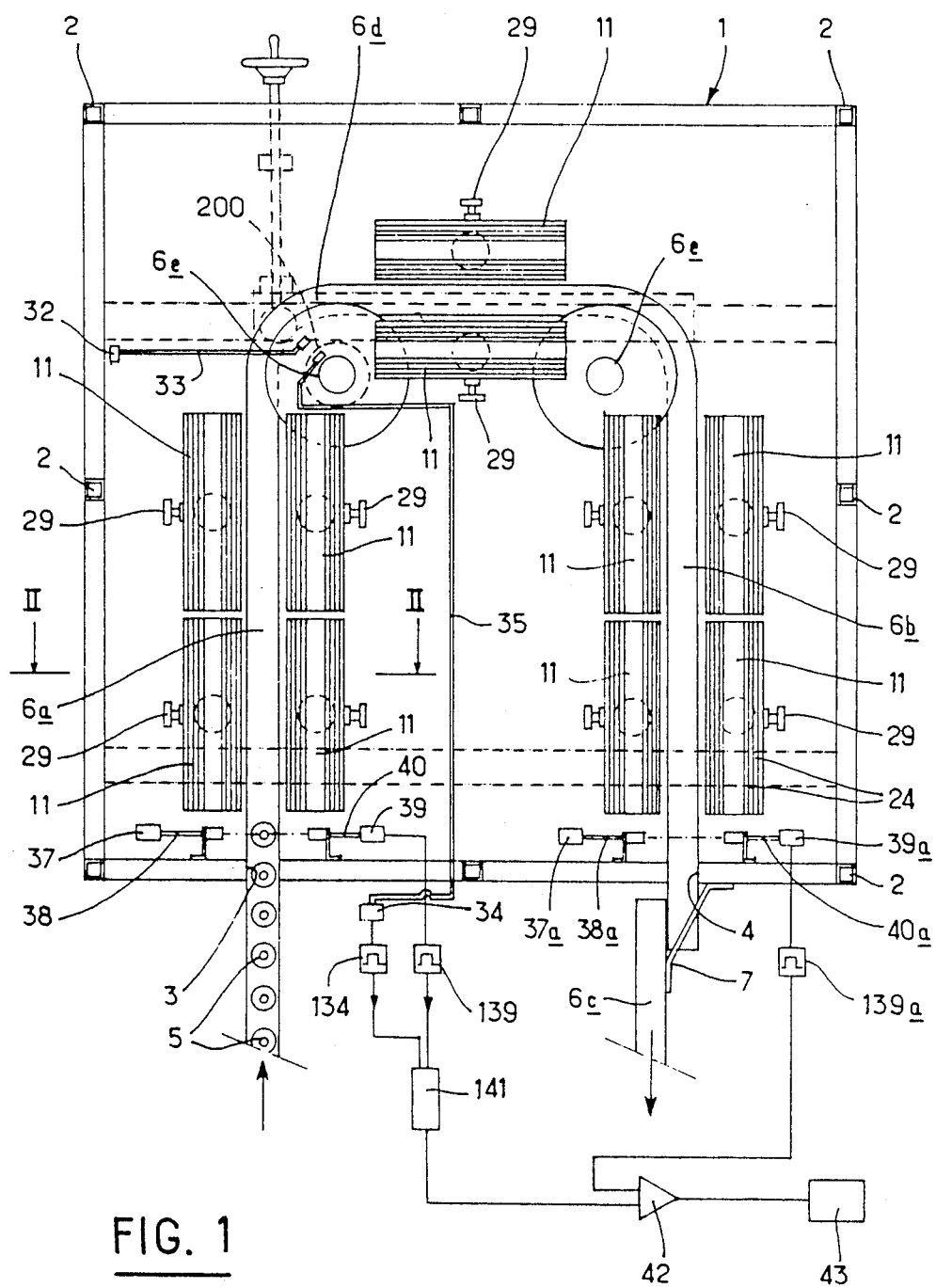
FIG. 1 is a schematic top view of the device according to the present invention, the detachable covers which are carried by the chassis to form therewith the tunnel-enclosure around the conveyor moves having been omitted so as to show the internal arrangement of the device of the invention; a diagram of the automatic monitoring device for the containers is also represented in FIG. 1.

If reference is now made to FIG. 1, it will be seen that 1 designates a fixed enclosure as a whole, constituted by a chassis 2 composed of metallic tubes and detachable cases, the covers not having been represented in the drawing; these cases are thermally insulated and are attached to the chassis 2 so as to form a tunnel comprising an inlet window 3 and an outlet window 4 for the passing of the containers 5 intended to be tested by the device. The median line of the tunnel is U-shaped.

As may be seen in FIG. 1, the containers 5 are placed behind each other on a conveyor 6 whose median line is also U-shaped and is identical with the median line of the tunnel.

The entry of the containers 6 into the enclosure is effected via one of the arms 6a of the U formed by the conveyor through the inlet window 3 and the emergence is effected via the other arm 6b through the outlet window 4.

Moreover, the outlet of the tunnel is fitted with a protective deflector 7 disposed slantingly in relation to the axis of this outlet so that the containers 5 emerging from the tunnel should be diverted by the deflector 7 and taken over by an arm 6c of the conveyor 6 outside the tunnel parallel to and adjacent to the arm 6b, the two arms 6b and 6c being adjacent in the region of the deflector 7.

Figure 2:
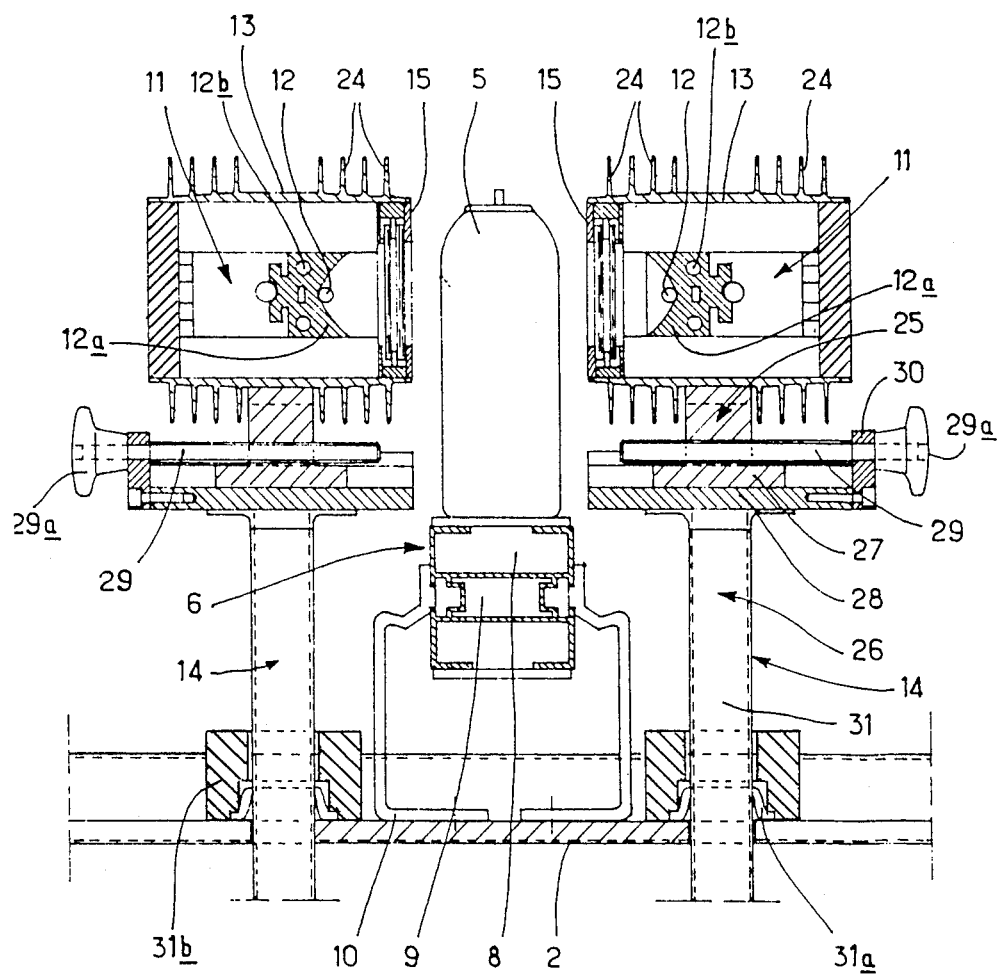
FIG. 2 is a vertical cross-section, on an enlarged scale, along II—II of FIG. 1.

As may be seen in FIG. 2, the conveyor 6 is constituted by pallets 8 on which the containers 5 rest, these pallets 8 being moved by a movable chain 9 mounted on a fixed support 10. Wheels 6e deflect the driving chain 9 at the two corners of the U; one of these wheels 6e constitutes the driving drum for the chain 6 and is associated with a slotted wheel 200. The conveyor 6 can be made of a plastic material because it is not heated by the infrared lamps 11 described below since the radiation is very directional.

Disposed in the enclosure 1 over and on either side of the path of the conveyor 6 are infrared lamps 11 which are ten in number and which are distributed as follows: four associated with the arm 6a, four associated with the arm 6b and two associated with the arm 6d constituting the web of the U, the lamps 11 being arranged in pairs, two lamps 11 of the same pair facing each other.

Figure 3:
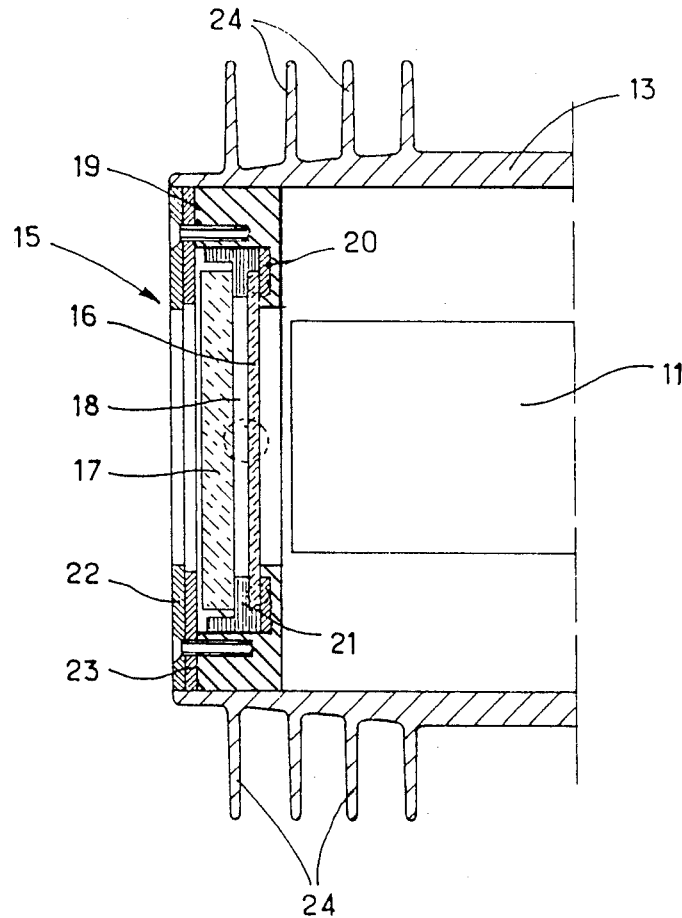
FIG. 3 is a view on a yet larger scale of the portion of FIG. 2 which represents the side of the casing of one infrared lamp which is transparent to the infrared radiations.

FIG. 2 illustrates the mounting of each of the lamps 11 and shows the facilities for adjusting its height on the one hand, and its distance in relation to the containers 5 on the other hand. Each lamp 11 (with an output of 2000 watts for example) is constituted by an infrared radiator 12 associated with a reflector 12a cooled by a water circuit 12b. Each lamp 11 is accommodated in a casing 13 integral with a base 14. The casing 13 of a lamp 11 has a parallelepipedonal shape whose longitudinal axis is disposed parallel to the arm of the conveyor 6 wherewith the said lamp 11 is associated. As may be seen in particular in FIG. 3, the side 15 of the casing 13 which is turned towards the conveyor 6 and in front of which the containers 5 will move, comprises two strips 16, 17, parallel to the longitudinal axis of the said casing 13, interspaced from each other so as to constitute an intermediate space 18, provision being made for this space to be swept by a compressed air flow (for example, at a relative pressure of 40,000 Pa). The internal strip 16 is a quartz strip, which is transparent to infrared radiation but having little resistance to thermal shocks. The external strip 17 is made of a glass of the type known under the brand name of "Pyrex", which is very impervious to thermal and mechanical shocks. The strips 17 prevent any damage to the lamps 11 in case one of the containers 5 carried in the tunnel could not withstand the pressure and were to explode in the tunnel.

The strips 16 and 17 are mounted in a plug 19 obturating the body of the casing 13, on the side 15 thereof. The internal strip 16 is applied against a sealing ring 20 inserted in the opening of the body of the casing 13, the ring 20 bearing against the plug 19 and receiving internally a distance piece 21 ensuring that a space is kept between the strips 16 and 17; the external strip 17 is held by an external frame 22 with the interposition of a plate 23, the assembly 22-23 being screwed on to the front side of the plug 19.

Moreover, the body of the casing 13 comprises external cooling fins 24 disposed in planes parallel to the longitudinal axis of the casing 13.

The base 14 is made in two parts, the one, 25, being connected to the casing 13 and the other, 26, being fixed to the chassis 2. The opposed end elements 27 and 28 respectively of the parts 25 and 26 have the shape of plates capable of sliding on each other, these plates being disposed in planes parallel to the longitudinal axis of the casing 13 and to the plane of displacement of the chain 9.

The part 25 is traversed by a threaded rod 29 which is perpendicular to the longitudinal axis of the casing 13 and which carries on the opposite side to the face 15 of the casing 13, a butterfly nut 29a allowing the distance of the casing 13 to be adjusted in relation to the median line of the conveyor 6. The rod 29 is carried by a flange 30 integral with the plate 28 of the part 26 of the base 14.

The plate 28 is integral with a foot 31 displaceable in height in relation to the chassis 2. The foot 31 can slide in an opening of the chassis; it is locked at the desired height by a fastening 31a disposed in a seat 31b, this locking being ensured on a frame which is not shown in FIG. 2.

The unit described above comprises an automatic monitoring means which is intended to ensure that each container 5 entering the tunnel leaves it after a given advance of the conveyor 6, otherwise a safety device is triggered. This monitoring means comprises on the one hand, a means indexing the advance of the conveyor 6 step by step and on the other hand, detector means intended to determine the presence or absence of a pressurized container 5 over a zone having the length of one indexed step.

Figure 4:
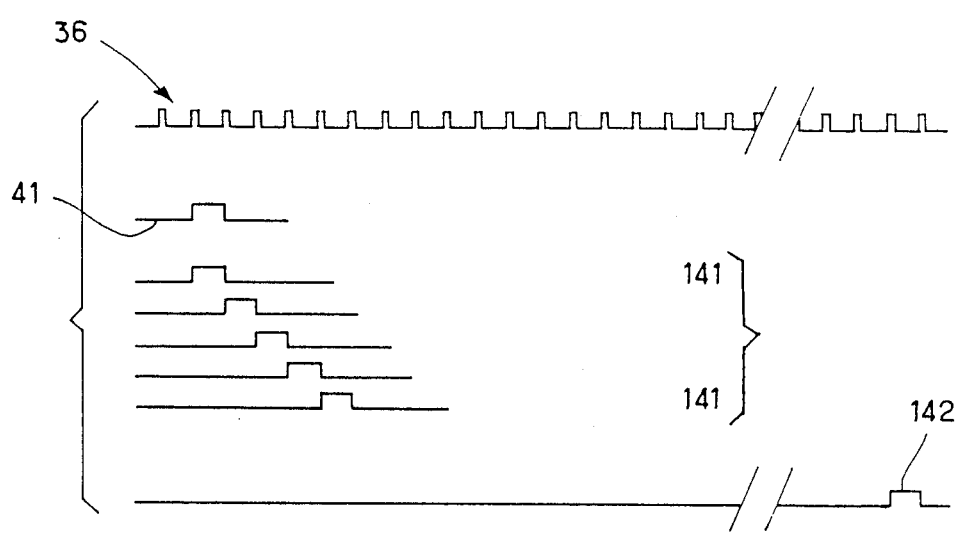
FIG. 4 is a diagram representing the electric signals emitted by the monitoring device.

The above indexing means is constituted by an optical transmitter-receiver disposed outside the tunnel near the driving drum for the conveyor. This transmitter-receiver comprises, on one side of the slotted wheel 200 integral with the drum driving the conveyor 6, a photodiode 32 associated with a bundle of optical fibres 33 and on the other side of the said slotted wheel, a receiving phototransistor 34 also associated with a bundle of optical fibres 35, the ends of the optical fibres 33, 35 being situated opposite each other so that each time a slot of the wheel passes in front of them, i.e. after one advance step of the conveyor 6, the luminous beam should not be obscured. In that case the phototransistor 34 emits a signal which is converted by a pulse shaper 134; the pulse obtained is designated by the reference numeral 36 in the diagram of FIG. 4.

The detector means at the tunnel inlet is constituted by an optical transmitter-receiver disposed within the said tunnel, just behind the window 3. It is constituted on the one hand by a photodiode 37 associated with a bundle of optical fibres 38, and on the other hand, by a receiving phototransistor 39 also associated with a bundle of optical fibres 40, the ends of the optical fibres 38 and 40 being disposed opposite each other on either side of the conveyor 6 so that each time the valve of a container 5 passes in front of them, the beam is obscured and the phototransistor 39 emits a signal which is converted by a pulse shaper 139 into rectangular voltage signal; this rectangular signal is designated by 41 in the diagram of FIG. 4. The widths of the rectangular signals 41 is less than the distance separating two pulses 36.

The detector means at the tunnel outlet disposed behind the outlet window 4 has a structure which is strictly identical with that of the detector means at the inlet; the elements composing them are, therefore, identical with those of the detector means at the inlet and are marked by the same reference numerals followed by the letter a.

The entry detection signal levels are sent to a register with time delay whose function is to delay the relevant indexing of each signal level by n pulses, n being the number of steps which the conveyor 6 must execute to convey a container 5 from the inlet to the outlet of the tunnel. Thus a signal level sent to the register with time delay 141 is displaced by one stop with each pulse 36 coming from the phototransistor 34, so that once it has been subjected to n displacements in the register with time delay 141, it is reencountered at the outlet of the register. The output is compared with the corresponding output of the phototransistor 39a, in a comparator 42. The displacement of the rectangular signals in the register with time delay 141 is schematically outlined in the diagram of FIG. 4.

The two inputs applied to the comparator 42 are identical. This corresponds to the case where the corresponding container 5 has correctly followed its path on the conveyor 6 in the tunnel (one rectangular signal is present at each input) or in the case where no container 5 was present in the corresponding zone of the conveyor 6 (absence of a rectangular signal on each input). On the other hand, if the two inputs of the comparator 42 are not identical, the output of the comparator 42 supplies a rectangular voltage signal 142 as represented on the last line of FIG. 4. The signal 142 triggers a safety device 43 which causes the lamps 11 to be extinguished and the conveyor 6 to be stopped.

There is, however, one case in which this monitoring system could give a faulty indication; this is the case of a jam starting from down the line. In fact, if a container 5 stops in front of the optical fibre bundle 38a and oscillates in front of it, and if one of the edges of the valve cuts the beam intermittently, the same transmission of signals may take place from the phototransistor 39a as in the case where the containers 5 move normally. This is why two other time delayed transmitter-receivers (not shown) are associated with the optical detection transmitter-receiver at the outlet from the enclosure 1, the unduly prolonged obscuring of either of these producing the triggering of the safety device 43. A jam may also be identified if one of the cells is occulted for a time exceeding a predetermined period.

Before starting, it is necessary to check that all the cells are functioning, by means of an automatic sequence control.

The device according to the invention can also be fitted, along the three axes of the conveyor 6, with a flame detector sensitive to UV radiations. If a defective container 5 explodes in the tunnel and if the temperature results in spontaneous combustion of the vapours thus released, the flame detector actuates the opening of a container filled with a pressurized non-combustible gas; this gas occupies the whole internal space of the tunnel in a fraction of a second; thus any fire risk is stopped.

It shall be duly understood that the embodiment described above is in no way restrictive and may give rise to any desirable modifications without thereby departing from the scope of the invention.

I claim:

1. In a device for the continuous hot testing of the mechanical strength of each pressurized container of a series of pressurized containers, said device comprising:
   (a) a fixed enclosure;
   (b) a conveyor for displacing the containers to be tested translationally in relation to the fixed enclosure; and
   (c) heating means within the enclosure, the containers traversing said enclosure in use of the conveyor so that their internal temperature is raised by said heating means up to a predetermined value; the improvement wherein:
   said enclosure traversed by the containers to be tested forms a tunnel;
   said heating means within said enclosure are constituted by a plurality of infrared lamps, each of which is protected by a casing having one side transparent to the emitted radiation; and
   said device includes an automatic monitoring device effective to ensure that each container which enters the tunnel emerges therefrom after a given advance of the conveyor and to trigger a safety device in the absence of such a container.

2. A device according to claim 1, wherein the outlet of the tunnel includes a protective deflector, slanting in relation to the axis of t e outlet; and wherein the conveyor follows the layout of said deflector after emerging from the tunnel.

3. A device according to claim 1, wherein the casing associated with each infrared lamp is a cooled metallic casing, said side transparent to the emitted infrared radiation comprising, on the one hand, towards the interior of the casing a quartz strip and, on the other hand, towards the outside of the casing a glass strip impervious to thermal shocks.

4. A device according to claim 3, including means circulating a cooling fluid through the space between the strips.

5. A device according to claim 3, wherein each infrared lamp casing is provided with external cooling fins.

6. A device according to claim 4, wherein said cooling fluid circulated through the space between the strips is compressed air.

7. A device according to claim 1, wherein the conveyor has a median line in the form of a U, the entry of the containers into the enclosure being effected via a first arm of the U, and the emergence via the second arm; and wherein the infrared lamps are disposed on either side of the conveyor all along the path thereof in the enclosure.

8. A device according to claim 1, wherein the median line of the conveyor is substantially rectilinear.

9. A device according to claim 1, wherein the monitoring device comprises:- means for indexing the advance of the conveyor step by step, and at the inlet and outlet of the enclosure detector means for determining the presence or absence of a pressurized container over a zone having the length of one step of the indexing advance of the conveyor.

10. A device according to claim 9, wherein the indexing and detector means include optical transmitter-receivers.

11. A device according to claim 10, wherein each optical transmitter-receiver of the detector means comprises:
    (a) a photodiode associated with a bundle of optical fibres having a first end adjacent the photodiode, and a second end remote therefrom; and
    (b) a receiving phototransistor associated with a further bundle of optical fibres having a first end adjacent the phototransistor, and a second end remote therefrom, said second ends of the fibre bundles facing one another and being separated by the conveyor.

12. A device according to claim 10, wherein the optical transmitter-receiver of the detector means comprises a photodiode, a first bundle of optical fibres having a proximal end adjacent the photodiode and a distal end, a receiving phototransistor, and a second bundle of optical fibres having a proximal end adjacent the phototransistor and a distal end, and interruptor means displaced by the conveyor and disposed between the distal ends of said optical fibre bundles, said distal ends facing one another.

13. A device according to claim 9, wherein the indexing means comprises a slotted wheel and means supplying a pulse when a slot of the slotted wheel integral with the drum driving the conveyor passes a fixed point, the passing from one slot to the next corresponding to one indexing step of the advance of the conveyor.

14. A device according to claim 13, wherein each time a container is identified the entry and emergence detector means supply a rectangular voltage signal of shorter duration than the time separating two successive pulses from the indexing means.

15. A device according to claim 14, including a register having a time delay, and means applying the rectangular signals of the entry detector means to said register with time delay where they are displaced by one stop with each pulse from the indexing means, and including means comparing (a) the signal level at one point of the register which corresponds, starting from the input of the register, to the number of indexing steps separating the entry and emergence detections, with (b) the level of the emergence detector means signal.

* * * * *